(12) United States Patent
Grass et al.

(10) Patent No.: US 11,395,702 B2
(45) Date of Patent: Jul. 26, 2022

(54) NAVIGATION SYSTEM

(71) Applicant: KONINKLIJKE PHILIPS N.V., Eindhoven (NL)

(72) Inventors: Michael Grass, Hamburg (DE); Neriman Nicoletta Kahya, Best (NL); Sven Prevrhal, Hamburg (DE); Marco Verstege, Eindhoven (NL); Eberhard Sebastian Hansis, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 777 days.

(21) Appl. No.: 14/914,016

(22) PCT Filed: Aug. 28, 2014

(86) PCT No.: PCT/EP2014/068219
§ 371 (c)(1),
(2) Date: Feb. 24, 2016

(87) PCT Pub. No.: WO2015/032676
PCT Pub. Date: Mar. 12, 2015

(65) Prior Publication Data
US 2016/0206381 A1 Jul. 21, 2016

(30) Foreign Application Priority Data

Sep. 6, 2013 (EP) .................................. 13183285

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/066* (2013.01); *A61B 2034/2051* (2016.02);
(Continued)

(58) Field of Classification Search
None
See application file for complete search history.

(56) References Cited

U.S. PATENT DOCUMENTS

| 6,415,167 B1 | 7/2002 | Blank et al. |
| 6,679,836 B2 | 1/2004 | Couvillon |

(Continued)

FOREIGN PATENT DOCUMENTS

| DE | 102011082444 | 12/2012 |
| JP | 2010194046 A | 9/2010 |

(Continued)

*Primary Examiner* — Jonathan Cwern

(57) ABSTRACT

The invention relates to a navigation system for navigating an interventional device (11) like a catheter and an interventional system comprising the navigation system. A position and shape determining unit (13) determines and stores a first position and shape of the interventional device within a living being (9) during a first interventional procedure like a first chemoembolization session and determines a second position and shape of an interventional device within the living being during a subsequent second interventional procedure like a second chemoembolization session. During the second interventional procedure the interventional device is navigated based on the stored first position and shape and based on the second position and shape. This allows considering during the second interventional procedure the path of the interventional device used during the first interventional procedure. In particular, this allows navigating the interventional device along the same path during the first and second interventional procedures.

15 Claims, 3 Drawing Sheets

(51) Int. Cl.
  *A61B 90/00*  (2016.01)
  *A61B 34/30*  (2016.01)
(52) U.S. Cl.
  CPC . *A61B 2034/2061* (2016.02); *A61B 2034/301* (2016.02); *A61B 2090/376* (2016.02)

(56) References Cited

U.S. PATENT DOCUMENTS

| | | |
|---|---|---|
| 7,343,195 B2 | 3/2008 | Strommer et al. |
| 7,772,541 B2 | 8/2010 | Froggatt et al. |
| 8,773,650 B2 | 7/2014 | Froggatt et al. |
| 8,965,072 B2 | 2/2015 | Fujii et al. |
| 2001/0031919 A1 | 10/2001 | Strommer et al. |
| 2007/0156019 A1 | 7/2007 | Larkin et al. |
| 2007/0185485 A1* | 8/2007 | Hauck ............... A61B 5/6885 606/41 |
| 2008/0002187 A1 | 1/2008 | Froggatt |
| 2008/0009714 A1* | 1/2008 | Oda ................. A61B 5/065 600/424 |
| 2008/0183074 A1 | 7/2008 | Carls et al. |
| 2009/0137952 A1 | 5/2009 | Ramamurthy et al. |
| 2009/0324161 A1 | 12/2009 | Prisco |
| 2010/0030063 A1 | 2/2010 | Lee et al. |
| 2010/0249507 A1 | 9/2010 | Prisco |
| 2011/0230758 A1 | 9/2011 | Eichler |
| 2012/0197097 A1* | 8/2012 | Chan ................ A61B 1/00165 600/342 |
| 2013/0303893 A1* | 11/2013 | Duindam ............. A61B 5/066 600/424 |
| 2013/0324833 A1 | 12/2013 | Barley et al. |
| 2013/0325387 A1 | 12/2013 | Manzke et al. |
| 2014/0088413 A1 | 3/2014 | Von Bucsh et al. |
| 2014/0243660 A1 | 8/2014 | Klinder et al. |

FOREIGN PATENT DOCUMENTS

| | | |
|---|---|---|
| JP | 2011050621 A | 3/2011 |
| JP | 2011104056 A | 6/2011 |
| WO | 2008115375 A1 | 9/2008 |
| WO | 2012035492 | 3/2012 |

* cited by examiner

NAVIGATION SYSTEM

CROSS-REFERENCE TO PRIOR APPLICATIONS

This application is the U.S. National Phase application under 35 U.S.C. § 371 of International Application Serial No. PCT/EP2014/068219, filed on Aug. 28, 2014, which claims the benefit of European Patent Application No. 13183285.9, filed on Sep. 6, 2013. These applications are hereby incorporated by reference herein.

FIELD OF THE INVENTION

The invention relates to a navigation system, a navigation method and a navigation computer program for navigating an interventional device like a catheter or a guidewire to a target region within a living being. The invention further relates to an interventional system comprising the navigation system.

BACKGROUND OF THE INVENTION

A transarterial chemoembolization (TACE) intervention generally comprises several interventional sessions, wherein in each of these interventional sessions a catheter is navigated to a part of the hepatic artery providing a tumor with blood, wherein chemoembolization material is injected at the location to which the catheter has been navigated. The navigation of the catheter to the part of the hepatic artery providing the tumor with blood is generally relatively inaccurate such that it is difficult to ensure that in different interventional sessions the catheter is navigated along the same path to the same location. This can decrease the quality of the intervention.

SUMMARY OF THE INVENTION

It is an object of the present invention to provide a navigation system, a navigation method and a navigation computer program for navigating an interventional device to a target region within a living being, which allow for an improved intervention. It is a further object of the present invention to provide an interventional system comprising the navigation system.

In a first aspect of the present invention a navigation system for navigating an interventional device to a target region within a living being is presented, wherein the navigation system comprises:

a position and shape determining unit for determining and storing a first position and shape of an interventional device within the living being during a first interventional procedure, wherein the position and shape determining unit is further adapted to determine a second position and shape of an interventional device within the living being during a subsequent second interventional procedure, and a navigation device for navigating the interventional device during the second interventional procedure based on the stored first position and shape and based on the second position and shape.

Since the navigation device is adapted for navigating the interventional device during the second interventional procedure based on the stored first position and shape, which has been determined during the first interventional procedure, and based on the second position and shape, which has been determined during the second interventional procedure, the path within the living being used during the first interventional procedure and the actual path of the interventional device determined during the second interventional procedure can both be considered, while navigating the interventional device during the second interventional procedure. For instance, if the determined second position and shape differs from the stored first position and shape, the navigation of the interventional device during the second interventional procedure can be corrected such that the position and shape of the interventional device during the second interventional procedure is similar to the position and shape of the interventional device during the first interventional procedure, in order to ensure that during the first interventional procedure and during the second interventional procedure the interventional device is navigated along the same path within the living being. This allows for an improvement of an intervention like a chemoembolization intervention comprising different interventional procedures, which may also be regarded as being different interventional sessions. This can further allow for a reduced time needed for the entire intervention, because the same path can be found in different interventional sessions faster.

The first interventional procedure and the second interventional procedure are part of an overall intervention. This overall intervention may span a number of days, with a relatively long period between the first interventional procedure and the second interventional procedure during which period the patient is typically not treated and leaves the interventional room. However, the overall intervention can also be performed in a shorter period with relatively short time or practically no time between the first interventional procedure and the second interventional procedure. In such a case, the overall intervention is essential a single, complex procedure and the first and second interventional procedures are interventional sessions of this complex procedure and the patient will be treated during this complex procedure substantially without interruption. Examples of such complex procedures are the procedures for placement of a stent like in EndoVascular Aortic Repair (EVAR) or Fenestrated Endovascular Aortic Repair (FEVAR) to treat aneurysms. These procedures include various intermediate sessions, i.e. first, second and potentially more interventional procedures, whereby the stored position and shape of an interventional device during one session can be used to navigate an interventional device during a further session.

The determined positions and shapes are preferentially three-dimensional positions and shapes describing three-dimensional paths, along which the interventional device is navigated during the first and second interventional procedures. The overall intervention can have more than two interventional procedures, wherein in all or in at least some of these interventional procedures the respective position and shape of the interventional device is determined, wherein the navigation device is adapted for navigating the interventional device during a current interventional procedure based on the position and shape determined during the current interventional procedure and on at least one stored position and shape determined during a previous interventional procedure for navigating the interventional device during the different interventional procedures along the same path.

The interventional device may be a vascular interventional device like a catheter, a guidewire, et cetera. The interventional procedures are preferentially percutaneous interventional procedures; in particular, they are preferentially parts of a TACE intervention.

The navigation device can be adapted for navigating the interventional device based on the entire respective position and shape or based on a part of the respective position and shape. For instance, the navigation device can be adapted for navigating the interventional device based on a part of the stored first position and shape and on the entire second position and shape.

In an embodiment the position and shape determining unit is adapted to determine the first and second positions and shapes by optical shape sensing. Determining the first and second positions and shapes by optical shape sensing allows determining these positions and shapes very accurately in a way, which is very simple for the user, i.e. the user does not need to handle different devices in a complicated way for determining the positions and shapes in the different interventional procedures.

The navigation device preferentially comprises a display for displaying the stored first position and shape and the second position and shape and a user interaction unit for allowing a user to move the interventional device during the second interventional procedure based on the displayed first and second positions and shapes. The navigation system may further comprise an imaging device for generating an image of the living being at least during the second interventional procedure, wherein the display may be adapted to show an overlay image showing the stored first position and shape and the second position and shape overlaid on the image. The imaging device is preferentially adapted to provide an x-ray projection image of the living being such that the stored first position and shape and the second position and shape can be shown on the x-ray projection image. Thus, a user can reliably navigate the interventional device during the second interventional procedure along a path being equal to the path along which the interventional device has been navigated during the first interventional procedure by observing the first and second positions and shapes of the interventional devices on the x-ray projection image.

In an embodiment the navigation device is adapted to compare the stored first position and shape with the second position and shape and to navigate the interventional device during the second interventional procedure based on the comparison. In particular, the navigation device can be adapted to automatically navigate the interventional device during the second interventional procedure such that the actual second position and shape is similar to at least a part of the first position and shape based on a comparison of the first and second positions and shapes.

It is further preferred that the position and shape determining unit is adapted to continuously determine the second position and shape during the second interventional procedure, wherein the navigation device is adapted for navigating the interventional device during the second interventional procedure depending on the stored first position and shape and the actual second position and shape. For instance, the second position and shape can be continuously determined in the second interventional procedure such that an overlay image can show the actual second position and shape together with the previously determined stored first position and shape on an x-ray projection image, which has been acquired in the second interventional procedure and which may be an actual image of the living being, in order to allow a user to navigate the interventional device during the second interventional procedure based on the live overlay image.

Preferentially, the position and shape determining unit is adapted to determine and store the first position and shape of the interventional device, when the interventional device has reached the target region during the first interventional procedure. Thus, the entire length of the path, which is defined by the position and shape of the interventional device during the first interventional procedure, when the interventional device has reached the target region, can be stored and used for navigating the interventional device during the second interventional procedure, in order to navigate the interventional device during the second interventional procedure along the entire path used during the first interventional procedure.

Moreover, the position and shape determining unit can be adapted to determine and store several first positions and shapes of the interventional device, while the interventional device is moved during the first interventional procedure, wherein at least one first position and shape is determined and stored, before the interventional device has reached the target region. For instance, the position and shape determining unit can be adapted to determine and store a first position and shape, when the interventional device has reached the target region in the first interventional procedure, and at least one further first position and shape, before the interventional device has reached the target region in the first interventional procedure. For example, a first position and shape can be determined and stored, before the interventional device has reached the target region in the first interventional procedure, when it has reached a critical location within the living being like a vascular branch point.

The navigation system may comprise a user interface allowing a user to indicate when the first position and shape should be stored, wherein the position and shape determining unit can be adapted to store the first position and shape, when the user has indicated that the first position and shape should be stored. The user can indicate that the first position and shape should be stored at several times during the first interventional procedure, in order to store several first positions and shapes of the interventional device during the first interventional procedure. For instance, the user may prompt the navigation system to store a first position and shape during the first interventional procedure, when the interventional device has reached a critical location within the living being like a vascular branch point.

The navigation device may also comprise a user interface allowing a user to indicate a part of the stored first position and shape, wherein the navigation device can be adapted for navigating the interventional device during the second interventional procedure based on the indicated part of the stored first position and shape and the second position and shape. In particular, the navigation device may comprise a display for displaying the stored first position and shape, wherein the user interface may be adapted to allow the user to mark on the displayed stored first position and shape a part of the first position and shape for indicating the same. For instance, if the interventional device is inserted at similar points in an artery in a person's groin in the first and second interventional procedures, while targeting different vascular end points in the first and second interventional procedures, the user may mark the point on the original path, i.e. on the stored first position and shape of the interventional device, up to which the user wants to follow the first position and shape. Or, when inserting the interventional device from the left instead from the right groin, the stored first position and shape may be marked starting from the aorta, i.e. the path of the interventional device may be reused, once the aorta is reached during the second interventional procedure.

In an embodiment the position and shape determining unit is adapted to a) register the stored first position and shape and the second position and shape to each other such that a similarity measure, which is indicative of a degree of similarity between the stored first position and shape and the second position and shape, is maximized, and b) determine whether during the first and second interventional procedures the navigation is performed along the same path based on the maximized similarity measure. For instance, if the maximized similarity measure is smaller than a predefined threshold, it can be determined that the navigation is performed along different paths during the first and second interventional procedures. The similarity measure can be based on, for instance, the Euclidean distance, a correlation, et cetera.

In an embodiment the navigation system further comprises an inner structure providing unit for providing an inner structure of the living being, wherein the navigation device comprises a display for displaying the inner structure together with the stored first position and shape and the second position and shape. In particular, the system can be adapted such that the part of the inner structure from an entry location of the interventional device, at which the interventional device has entered the living being in the second interventional procedure, to a location of a tip of the interventional device as indicated by the second position and shape of the interventional device is displayed. The inner structure may be provided by providing a roadmap of the vascular system within the living being. The display may then be adapted to display the part of the roadmap from the entry location of the interventional device, at which the interventional device has entered the vascular system of the living being in the second interventional procedure, to the location of the tip of the interventional device as indicated by the second position and shape of the interventional device, in order to display the part of the roadmap, which is currently relevant for navigating the interventional device during the second interventional procedure. The system may be adapted to only display the part of the inner structure from the entry location of the interventional device, at which the interventional device has entered the living being in the second interventional procedure, to the location of the tip of the interventional device as indicated by the second position and shape of the interventional device on the display and to not show additionally the remaining part of the inner structure. However, the system can also be adapted to show the entire inner structure and to display the part of the inner structure from the entry location of the interventional device to the location of the tip of the interventional device as indicated by the second position and shape of the interventional device by highlighting this part with respect to the remaining part of the inner structure. For instance, the part to be displayed can be shown with a higher intensity or with a color which is different to a color of the remaining part of the inner structure.

The position and shape determining unit may be adapted to determine and store in the first interventional procedure the position and shape of a first interventional device as the stored first position and shape and to determine in the second interventional procedure the position and shape of a second interventional device as the second position and shape, wherein the navigation device may be adapted for navigating the second interventional device during the second interventional procedure based on the stored first position and shape and the second position and shape. Thus, in the first and second interventional procedures different interventional devices may be used. However, in another embodiment also the same interventional device may be used in the first and second interventional procedures.

In a further aspect of the present invention an interventional system for applying an interventional procedure to a living being is presented, wherein the interventional system comprises:

an interventional device for performing the interventional procedure, and a navigation system for navigating the interventional device to a target region within the living being as defined in claim 1.

In another aspect of the present invention a navigation method for navigating an interventional device to a target region within a living being is presented, wherein the navigation method comprises:

determining and storing a first position and shape of an interventional device within the living being during a first interventional procedure and determining a second position and shape of an interventional device within the living being during a subsequent second interventional procedure, and navigating the interventional device during the second interventional procedure based on the stored first position and shape and based on the second position and shape.

In a further aspect of the present invention a navigation computer program for navigating an interventional device to a target region within a living being is presented, wherein the navigation computer program comprises program code means for causing a navigation system as defined in claim 1 to carry out the steps of the navigation method as defined in claim 14, when the navigation computer program is run on a computer controlling the navigation system.

It shall be understood that the navigation system of claim 1, the interventional system of claim 13, the navigation method of claim 14 and the navigation computer program of claim 15 have similar and/or identical preferred embodiments as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
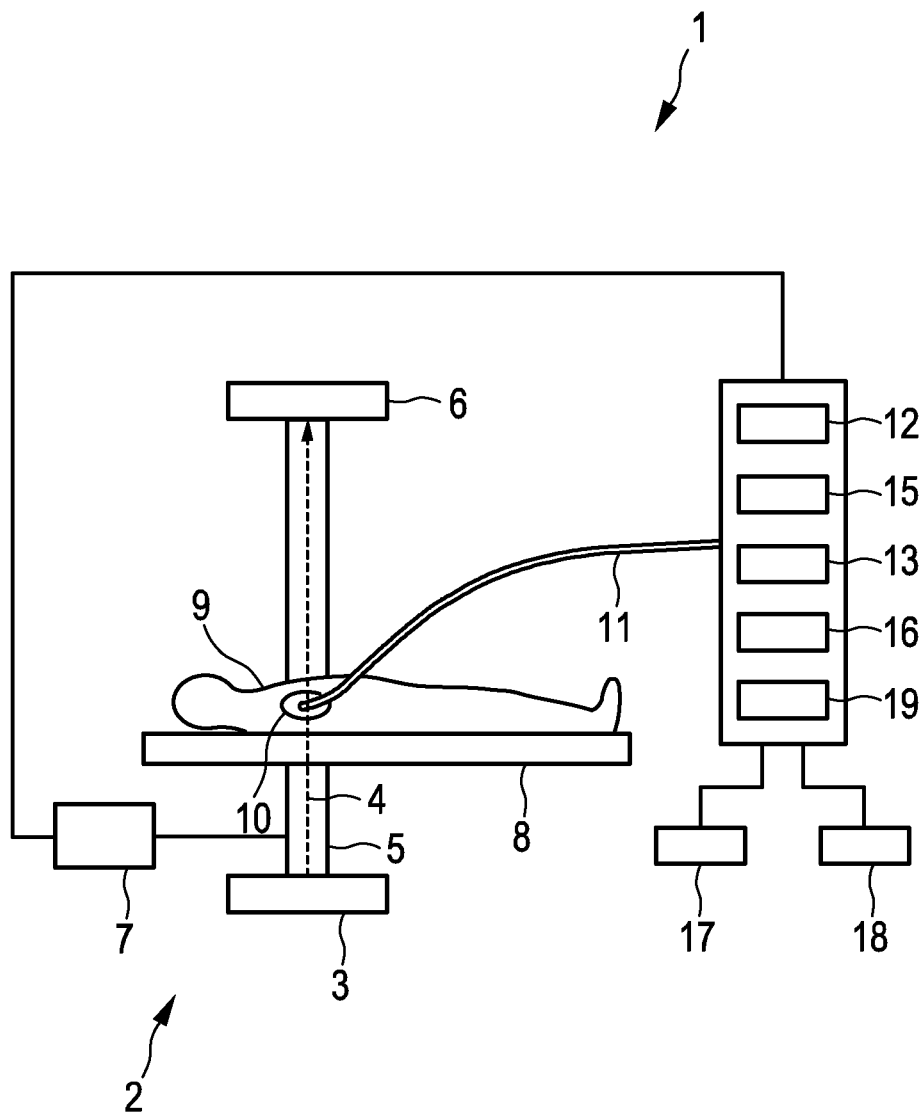
FIG. 1 shows schematically and exemplarily an interventional system for applying an interventional procedure to a living being.

FIG. 1 shows schematically and exemplarily an embodiment of an interventional system for applying an interventional procedure to a living being. In this embodiment the interventional system 1 is adapted to perform a TACE intervention. The interventional system 1 comprises a catheter 11 for being navigated to the hepatic artery of a person 9 lying on a support means like a table 8. The catheter 11 is preferentially navigated from the right groin through the femoral artery, the abdominal aorta and the celiac trunk to the common hepatic artery. The catheter 11 is preferentially adapted to be navigated via a user interaction unit 12 by a user like a physician.

For instance, the catheter 11 can comprise several portions, which are connected by hinges such that the portions are pivotable with respect to each other by using wires connected to the respective portions. In particular, one end of a respective wire can be connected to a respective portion of the catheter 11 and the other end of the respective wire can be connected to a respective motor of the user interaction unit 12 such that the different portions of the catheter 11 can be pivoted with respect to each other via the wires and the motors in the user interaction unit 12. The user interaction unit 12 can comprise at least two further motors for translating the entire catheter 11 and for rotating the entire catheter 11. For translating and rotating the entire catheter 11 the user interaction unit 12 may comprise a mechanical fixture for clamping the catheter 11, wherein the at least two further motors may be adapted to translate the mechanical fixture along a rail and to rotate the mechanical fixture. As an alternative to rotating the mechanical fixture, the user interaction unit 12 may be configured such that the catheter 11 is rotated within the mechanical fixture by using at least one of the further motors. Generally, mechanical configurations of known robotic systems can be used for modifying the shape of the catheter 11 and moving the catheter 11 like the mechanical configuration of the Magellan robotic system from the company Hansen. The user interaction unit 12 may be used by the physician via an input unit 17 comprising a keyboard, a computer mouse, a touchpad, a joystick and/or another input means for allowing the user to input desired navigation commands into the user interaction unit 12. In other embodiments the shape of the catheter may be modified and the catheter may be moved in another way by using, for instance, magnetic means. Moreover, in a further embodiment the catheter may be directly manually steered by using guidewires.

The interventional system further comprises a position and shape determining unit 13 for determining the position and shape of the catheter 11 within the person 9. In this embodiment the position and shape determining unit 13 is adapted to use optical shape sensing for determining the position and shape of the catheter 11. For instance, the position and shape determining unit 13 can be adapted to use the technique disclosed in U.S. Pat. No. 7,772,541 B2, the technique disclosed in EP 2 478 331 A2 or another optical shape sensing technique for determining the position and shape of the catheter 11.

After the tip of the catheter 11 has reached the hepatic artery, small embospheres, which are particles designed to block blood vessels and which are coated with chemotherapeutic drugs, are injected directly into an artery supplying a tumor 10 via the catheter 11 by using a treating unit 19. The treating unit 19 comprises a reservoir of the embospheres and a pump for transferring the embospheres via the catheter 11 to the hepatic artery. In another embodiment the treating unit can also be adapted to inject another kind of particles like small spheres, which do not comprise a chemotherapeutic drug and which are just used for clogging desired vessels, or like small spheres with a radiation source like Y90 for performing a selective internal radiation therapy (SIRT).

The injected embospheres restrict the tumor's arterial blood supply and the chemotherapeutic agent is delivered directly to the target tissue, thereby locally concentrating the chemotherapeutic agent in the area of the tumor, which leads to decreased chemotherapeutic side effects compared to systemic chemotherapy. The TACE, i.e. the injection of the embospheres, is performed in several interventional sessions, wherein between these several interventional sessions the catheter 11 may be completely removed from the person 9. Moreover, for different interventional sessions, which may also be regarded as being different interventional procedures, the same catheter 11 or different catheters may be used. In this embodiment for a first interventional session and a subsequent second interventional session the same catheter 11 is used, wherein the position and shape determining unit 13 is adapted to determine and store a first position and shape of the catheter 11 within the person 9 during the first interventional session and to determine a second position and shape of the catheter 11 within the person 9 during the second interventional session.

The first position and shape determined during the first interventional session is stored such that it can be shown on a display 18 during the second interventional session together with the actually determined second position and shape of the catheter 11, in order to allow the user to navigate the catheter 11 during the second interventional session along the same path as used during the first interventional session, i.e. along the path indicated by the stored first position and shape of the catheter 11 determined during the first interventional procedure. In particular, the second position and shape can be determined continuously during the second interventional procedure, while the catheter 11 is moved to the hepatic artery, while the respective actual second position and shape of the catheter 11 can be shown on the display 18 together with the stored first position and shape determined during the first interventional procedure, in order to allow the user to navigate the catheter 11 during the second interventional procedure along the path within the person 9 used during the first interventional procedure.

The position and shape determining unit 13 is adapted to register the actual second position and shape during the second interventional session with a corresponding part of the stored first position and shape. In particular, if the actual second position and shape defines a path having a certain length, this actual second position and shape can be registered with a corresponding part of the stored first position and shape defining a path having the same length. If during the second session the catheter has reached the target region, the corresponding entire second position and shape may be registered with the entire stored first position and shape.

The position and shape determining unit 13 is adapted to register the determined and stored first position and shape to the determined second position and shape by using known registration algorithms like known 3D-3D registration algorithms. The position and shape determining unit 13 may also be adapted to allow a user to manually register the first and second positions and shapes and/or to perform the registration based on well-defined points used by both paths defined by the first and second positions and shapes like the skin entry point. Also a combination of these registration techniques may be used.

The position and shape determining unit 13 can be adapted to use a similarity measure for registering the first and second positions and shapes to each other, wherein the registration algorithm can be adapted to register the first and second positions and shapes to each other such that the similarity measure is maximized. If the maximized similarity measure is smaller than a predefined threshold, it may be assumed that the first and second positions and shapes define different paths within the person, which is preferentially indicated on the display 18. The similarity measure can be based, for instance, on the Euclidean distance, a correlation, et cetera.

The interventional system 1 further comprises an imaging device 2 for generating an image of the person 9 during the intervention, wherein the display 18 is adapted to show an overlay image showing the first position and shape and the second position and shape overlaid on the image generated by the imaging device 2. In this embodiment the imaging device 2 is a C-arm x-ray system for generating an x-ray projection image. The C-arm x-ray system 2 comprises a C-arm 5, wherein at opposing ends of the C-arm 5 an x-ray source 3 and an x-ray detector 6, respectively, are mounted. The x-ray source 3 is adapted to emit x-rays 4 traversing the person 9 and the x-ray detector 6 is adapted to detect the x-rays 4 after having traversed the person 9. The C-arm is movable, in particular, rotatable and translatable, in order to generate x-ray projection images in different projection directions. The C-arm x-ray system 2 further comprises a control unit 7 for controlling the C-arm x-ray system, in particular, for controlling the x-ray source 3 and the x-ray detector 6. The control unit 7 is also adapted to generate the x-ray projection images based on detection values, which are indicative of the x-ray intensities detected by the x-ray detector 6 and which are received from the x-ray detector 6.

The interventional system 1 further comprises a user interface allowing a user to indicate when the first position and shape should be stored, wherein the position and shape determining unit 13 is adapted to store the first position and shape, when the user has indicated that the first position and shape should be stored. In this embodiment the user interface is the input unit 17, which allows the user to input into the interventional system that the actual first position and shape of the catheter 11 should be stored. Thus, the position and shape determining unit 13 can be adapted to continuously determine the first position and shape during the first interventional session, wherein the continuously determined first position and shape can be stored only, if this has been indicated by the user by using the user interface 17. Preferentially, the first position and shape is stored, when the catheter 11 has reached the target region being, in this embodiment, the hepatic artery, in order to store the entire path used during the first interventional session. Storing the first position and shape of the catheter 11 during the first interventional session, when the catheter 11 has reached the target region, allows navigating the catheter 11 during the second interventional session along the entire path used during the first interventional session. In addition, the system can be adapted to allow the user to mark certain regions on the stored first position and shape during the first interventional session or after the first session has been completed by using a user interface 15. For instance, the user can indicate via the user interface 15 regions of the stored first position and shape of the catheter 11, which should be marked. These regions may comprise critical locations within the person 9 like vascular branch points. The system can be adapted to allow the user to mark these regions, after the catheter 11 has reached the target region and after the first position and shape of the catheter 11 has been stored, directly on this stored first position and shape shown on the display 18, or the system may be adapted to allow the user to indicate the respective region, when the tip of the catheter 11 has reached the respective region during the first interventional session, wherein this indicated respective region can finally be marked on the stored first position and shape. During the second interventional session the marked regions can be shown on the display 18. Moreover, further first positions and shapes can be stored, before the catheter 11 has reached the target region. For instance, the user can indicate via the user interface 15 that a first position and shape of the catheter 11 should be stored, when the catheter 11 has reached a critical location within the person 9 like a vascular branch point.

In another embodiment the position and shape determining unit 13 can also be adapted to automatically store the first position and shape, when the catheter 11 has reached the target region during the first interventional session. For instance, the position of the target region can be automatically determined based on a pre-acquired image of the person 9 like a computed tomography image or a magnetic resonance image or a user can mark the target region on such an image, wherein based on the position of the target region and the continuously determined first position and shape during the first interventional session it can be determined, when the catheter 11 has reached the target region, wherein then the first position and shape of the catheter 11 can be stored.

The user interface 15 may further be adapted to allow the user to indicate a part of the stored first position and shape, which should be shown on the display 18 alone, i.e. without the remaining part of the stored first position and shape, or which should be shown in a highlighted way with respect to the remaining part of the stored first position and shape, in order to allow the user to navigate the catheter 11 during the second interventional session based on the indicated part of the stored first position and shape and the actual second position and shape by using the user interaction unit 12.

In particular, for indicating the part of the stored first position and shape the display 18 may display the entire stored first position and shape, wherein the user interface 15 may be a graphical user interface allowing the user to mark on the displayed stored entire first position and shape the part of the first position and shape, which should be used during the second interventional session. The input unit 17 may be used together with the graphical user interface 15 for indicating the part of the stored first position and shape. If the catheter 11 is inserted at similar points in an artery in the person's groin in the first and second interventional sessions, while targeting different vascular end points in the first and second interventional sessions, the user may mark the point on the original path, i.e. on the stored entire first position and shape of the catheter 11, up to the point where the user wants to follow the original path. Or, for instance, when inserting the catheter 11 from the left instead from the right groin, the stored entire first position and shape may be marked starting from the aorta, i.e. the original path from the catheter 11 may be reused only starting from the aorta.

The interventional system 1 further comprises an inner structure providing unit 16 for providing an inner structure of the person 9, wherein the display 18 may be adapted to display the provided inner structure together with the first and second positions and shapes of the catheter 11. This is schematically and exemplarily illustrated in FIG. 2.

Figure 2:
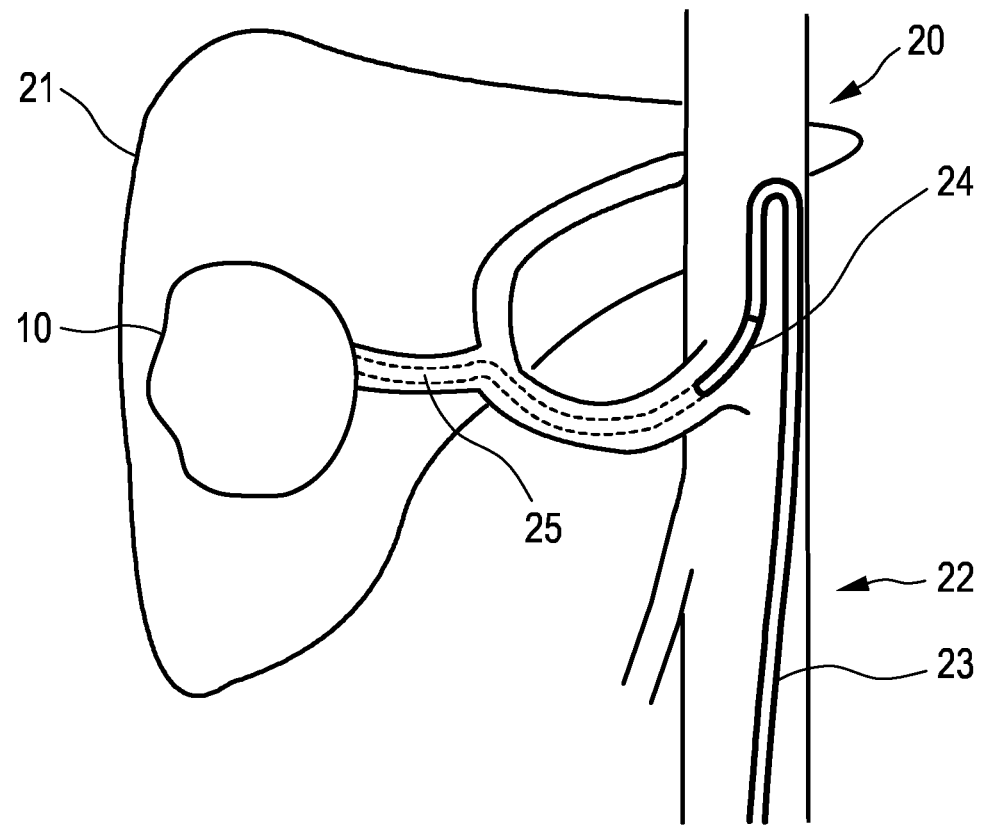
FIG. 2 shows schematically and exemplarily an inner structure of the living being together with positions and shapes of a catheter determined in different interventional procedures.

The inner structure 20 schematically and exemplarily shown in FIG. 2 includes vessels 22, the liver 21 and the tumor 10. The display 18 further shows the stored first position and shape 25, i.e. the original path used during the first interventional session, partly overlaid by the second position and shape 23, 24 of the catheter 11, which indicates the current position and shape of the catheter 11 during the navigation of the catheter 11 to the target region in the second interventional session. In FIG. 2 reference number 24 indicates the position and shape of the tip of the catheter 11 and reference number 23 indicates the position and shape of the remaining part of the catheter 11 during the second interventional session.

The interventional system can be adapted to show the entire inner structure 20 as illustrated in FIG. 2 or only a part of the inner structure 20 from the entry location of the catheter 11, at which the catheter 11 has entered the person 9 in the second interventional session, to a current location of the tip of the catheter 11 as indicated by the actual second position and shape of the catheter 11. The inner structure provided by the inner structure providing unit 16 may be a roadmap showing the vascular structure within the person 9, which indicates possible paths within the person 9, wherein the entire road map may be shown on the display 18 or only a part of the roadmap from the entry location of the catheter 11, at which the catheter 11 has entered the person 9 in the second interventional session, to the current location of the tip of the catheter 11 as indicated by the actual second position and shape of the catheter 11 in the second interventional session may be shown on the display 18.

Since the user interaction unit 12, the user interface 15, the input unit 17 and display 18 are used for navigating the catheter 11 during the second interventional session based on the stored first position and shape and based on the second position and shape, these components can be regarded as being components of a navigation device for navigating the catheter 11 during the second interventional session based on the stored first position and shape and based on the second position and shape. Moreover, since this navigation device is used together with the position and shape determining unit 13 for navigating the catheter 11 to the target region 10 within the person 9, the navigation device and the position and shape determining unit 13 can be regarded as being components of a navigation system for navigating the catheter 11 to the target region 10 within the person 9, which is integrated with the interventional system 1.

Figure 3:
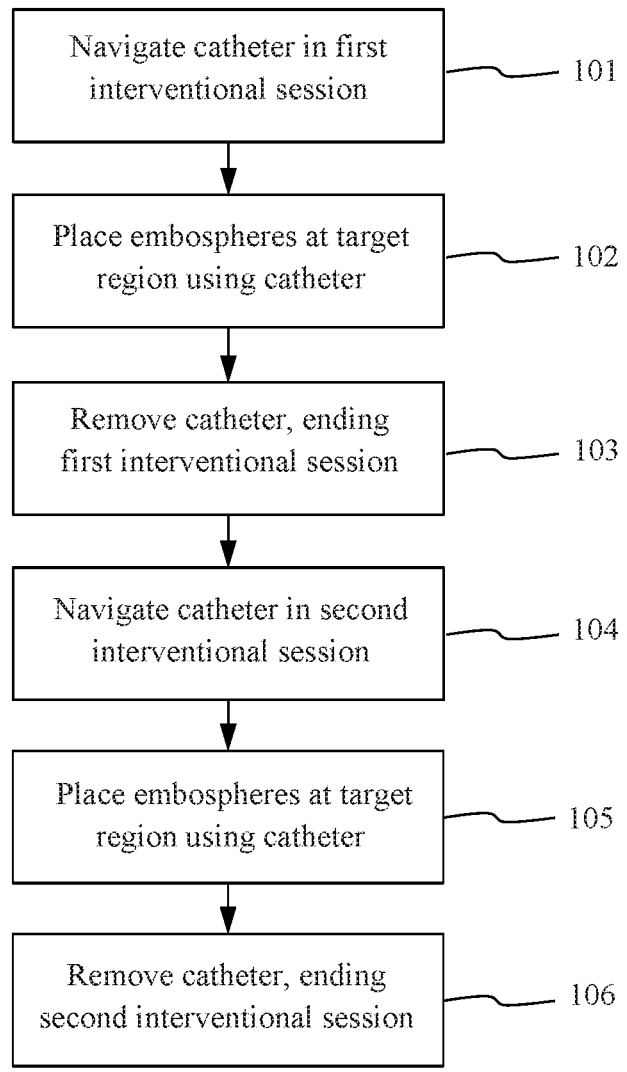
FIG. 3 shows a flowchart exemplarily illustrating an embodiment of an interventional method for applying an interventional procedure to a living being.

In the following an embodiment of an interventional method will be exemplarily described with reference to a flowchart shown in FIG. 3.

In step 101 in a first interventional session the catheter 11 is navigated to a part of the hepatic artery, which provides the tumor 10 with blood, wherein the position and shape of the catheter 11 is determined by optical shape sensing during this navigation. When the catheter 11 has reached the target region, where the chemoembolization material should be injected, the determined position and shape of the catheter 11 is stored as the first position and shape to be used during a subsequent second interventional session.

In step 102 embospheres are placed at the target region in the hepatic artery by using the treating unit 19 and the catheter 11. After the embospheres have been placed in the hepatic artery, the catheter 11 is removed from the person 9 in step 103 and the first interventional session ends.

In step 104 during a second interventional session the catheter 11 is navigated to the hepatic artery, while the position and shape of the catheter 11 is continuously determined as a second position and shape and shown on the display 18 together with the stored first position and shape. The respective actual second position and shape and the stored first position and shape may be shown overlaid on an x-ray projection image provided by the C-arm x-ray system 2 and/or on a representation of an inner structure 20 like a roadmap. By showing the stored first position and shape, i.e. the original path within the person 9, together with the respective actual second position and shape of the catheter 11 during the second interventional session on the display 18, the user can navigate the catheter 11 during the second interventional session along the original path used during the first interventional session by using the user interaction unit 12.

After the catheter 11 has been navigated along the original path such that the catheter 11 has reached the target location which has also been reached during the first interventional session, in step 105 embospheres are placed at the target location by using the catheter 11 and the treating unit 19. After the embospheres have been placed at the target location, the catheter 11 can be removed from the person 9 and the second interventional session ends in step 106.

Further interventional sessions, i.e. a third interventional session, a fourth interventional session, et cetera, can follow, wherein during the respective further interventional session a stored position and shape of the catheter 11 determined during a previous interventional session is used for navigating the catheter 11. Preferentially, for all interventional sessions following the first interventional session the position and shape of the catheter 11 determined and stored during the first interventional session is used as the original path.

Since steps 101 and 104 just refer to the navigation of the catheter to the target region, these steps can be regarded as forming a navigation method for navigating the catheter 11 to the target region within the person. Thus, the method described above with reference to FIG. 3 can be regarded as being an interventional method with an integrated navigation method.

Although in the embodiments described above with reference to FIGS. 1 to 3 the interventional device is a catheter, in other embodiments the interventional device can also be another device like a guidewire, wherein also in this case the position and shape determining unit is adapted to determine and store a first position and shape of the interventional device within the living being during a first interventional procedure and to determine a second position and shape of the interventional device within the living being during a subsequent second interventional procedure, wherein a navigation device is provided for navigating the interventional device during the second interventional procedure based on the stored first position and shape and based on the second position and shape.

Although in the embodiments described above with reference to FIGS. 1 to 3 the living being is a person, in other embodiments the living being can also be an animal. Moreover, although in the embodiments described above with reference to FIGS. 1 to 3 the respective position and shape has been determined by using optical shape sensing, in other embodiments other techniques can be used for determining the position and shape of the interventional device within the living being during the respective interventional procedure. For instance, the interventional device can comprise several electromagnetic tracking sensors arranged along its length for determining the position and shape of the interventional device.

Although in the embodiments described above with reference to FIGS. 1 to 3 the intervention is a TACE intervention, in other embodiments the intervention can be another intervention performed in different interventional sessions, i.e. having different interventional procedures. In particular, the intervention can be any intervention, in which it is important that a path used during a first interventional session is also at least partly used during a subsequent second interventional session. For instance, the intervention can be an ablation intervention, wherein in different ablation sessions at least partly the same path should be used, or it can be an injection intervention, wherein an injection device should be navigated along the same path in different injection sessions. The intervention can also be another embolization intervention like a uterine-fibroids embolization intervention or a prostate embolization intervention. Also diagnosing and treating pulmonary cancer can be performed in several sessions, wherein a flexible bronchoscope may be used for diagnosing and treating pulmonary tumors and wherein during the different sessions the bronchoscope should be navigated along the same path. The intervention can also be a placement of a stent, like in EndoVascular Aortic Repair (EVAR) or Fenestrated Endovascular Aortic Repair (FEVAR), in which the interventional device should be navigated along the same path in the different sessions of the intervention.

The three-dimensional tracking during the first interventional session, i.e. the determination of the first position and shape during the first interventional session, provides the information, which can be used to replicate intervention guidance in the same person in a follow-up interventional procedure. In the above described TACE intervention the catheter is positioned in a part of the hepatic artery providing the tumor with blood. From there the chemoembolization material is injected. This procedure is repeated several times during different interventional sessions. Guiding the user, who is supposed to be an interventional radiologist, along the same device path to the same vascular position during the different interventional sessions can improve the quality and speed of these interventions.

The interventional system described above with reference to FIG. 1 can be adapted to track the complete catheter shape and its position throughout the first catheter intervention, i.e. throughout the first interventional session. Then, the point in time may be marked and thereby the three-dimensional position and shape of the catheter may be stored, when the catheter has reached its target location, in particular, when the chemoembolization material is injected in the artery. The stored position and shape of the catheter can then be regarded as being the target position and shape, which should be achieved again in the second interventional session. The stored position and shape of the catheter, i.e. the first position and shape of the catheter, can be regarded as being a person specific catheter position and shape for this type of intervention for this person. Additional position and shape "snap shots" can be stored for later use at critical locations during the first interventional session, for instance, when the catheter tip reaches a vascular branch point. The position and shape defining the entire path to the target region and the optional further "snap shots" may be stored in a database, wherein during each following intervention the stored catheter positions and shapes can be loaded from the database and can be compared with the actual position and shape of the catheter during progression towards the target region. The one or several stored positions and shapes and the actual position and shape of the catheter can be displayed as a live overlay on x-ray projection images or they can be displayed directly, i.e. not being overlaid on an x-ray projection image. By comparing the different positions and shapes guidance can be given to the user how to move the catheter to match the recorded three-dimensional path most optimally.

The interventional system may also be adapted to partially reuse the original path, i.e. only a part of the stored first position and shape of the catheter determined during the first interventional session may be used for navigating the catheter during the second interventional session. For example, the catheter may be inserted at a comparable point in an artery in the patients groin while targeting a different vascular end point. Here, the user may mark the point on the original catheter path, i.e. on the stored first position and shape, up to the point where the user wants to follow it. Alternatively, for instance, when inserting the catheter from the left instead of the right groin, the catheter path, i.e. the stored first position and shape, may be reused, once the aorta is reached in the second interventional session.

Although in the embodiments described above with reference to FIGS. 1 to 3 the stored first position and shape, which has been determined during the first interventional session, is displayed together with an actual second position and shape of the catheter during the second interventional session, in order to allow the user to move the catheter during the second interventional session along the path, along which the catheter has also been moved during the first interventional session, in another embodiment the stored first position and shape of the catheter and the actual second position and shape of the catheter can also be used to automatically navigate the catheter to the target region along the path, which has been used during the first interventional session. Thus, the catheter 11 may be a catheter being automatically controllable by a catheter control unit depending on a comparison between the stored first position and shape and the actual second position and shape. In particular, in addition or as an alternative to the user interaction unit 12 the interventional system 1 may comprise the catheter control unit for automatically navigating the catheter during the second interventional session based on a comparison between the stored first position and shape of the catheter and the actual second position and shape.

Although in above described embodiments the first and second positions and shapes are three-dimensionally registered to each other, the first and second positions and shapes may also be four-dimensionally registered to each other. For instance, the first position and shape can be determined and stored together with a respective phase of a periodic movement of the person like a cardiac phase or a respiratory phase, wherein during the determination of the second position and shape also the cardiac phase or the respiratory phase can be determined and the second position and shape, which corresponds to the same phase as the phase stored with the first position and shape, can be registered with the stored first position and shape.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of a position and shape of an interventional device, a comparison of positions and shapes of the interventional device determined in different interventional sessions, et cetera performed by one or several units or devices can be performed by any other number of units or devices. These procedures and/or the control of the interventional system in accordance with the interventional method and/or the control of the navigation system in accordance with the navigation method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a navigation system for navigating an interventional device like a catheter and an interventional system comprising the navigation system. A position and shape determining unit determines and stores a first position and shape of the interventional device within a living being during a first interventional procedure like a first chemoembolization session and determines a second position and shape of an interventional device within the living being during a subsequent second interventional procedure like a second chemoembolization session. During the second interventional procedure the interventional device is navigated based on the stored first position and shape and based on the second position and shape. This allows considering during the second interventional procedure the path of the interventional device used during the first interventional procedure. In particular, this allows navigating the interventional device along the same path during the first and second interventional procedures.

The invention claimed is:

1. A navigation system for enabling navigating an interventional device to a target region within a living being, the navigation system comprising:
   a position and shape determining unit for determining and storing a first position and shape of an interventional device within the living being when the interventional device reaches the target region during a first interventional procedure using optical shape sensing, and for continuously determining a second position and shape of the interventional device within the living being during a subsequent second interventional procedure using optical shape sensing; and
   a navigation device comprising a display and a user interaction unit for enabling a user to navigate the interventional device along a selected path of a plurality of available paths through an anatomical structure to the target region during the first interventional procedure, the anatomical structure defining at least one branch point physically separating the available paths, for displaying the stored first positon and shape of the interventional device, and for further enabling the user to navigate the interventional device along the same path during the second interventional procedure by matching the second position and shape, which are determined and displayed while the interventional device is being navigated along the same path during the second interventional procedure, with the displayed first position and shape of the interventional device.

2. The navigation system as defined in claim 1, wherein the navigation system further comprises an imaging device for generating an image of the living being at least during the second interventional procedure, wherein the display further displays an overlay image showing the stored first position and shape and the second position and shape overlaid on the image.

3. The navigation system as defined in claim 1, wherein the navigation device compares the stored first position and shape with the second position and shape to enable navigating the interventional device along the same path during the second interventional procedure based on the comparison.

4. The navigation system as defined in claim 1, wherein the position and shape determining unit determines and stores the first position and shape of the interventional device when the interventional device has reached the target region during the first interventional procedure.

5. The navigation system as defined in claim 1, wherein the navigation system further comprises a user interface allowing the user to indicate when the first position and shape are stored, and wherein the position and shape determining unit stores the first position and shape indicated by the user.

6. The navigation system as defined in claim 1, wherein the navigation device further comprises a user interface for allowing the user to indicate a part of the stored first position and shape, and wherein the navigation device enables navigating the interventional device during the second interventional procedure based on the indicated part of the stored first position and shape and the second position and shape.

7. The navigation system as defined in claim 1, wherein the position and shape determining unit:
   registers the stored first position and shape and the second position and shape to each other such that a similarity measure, which is indicative of a degree of similarity between the stored first position and shape and the second position and shape, is maximized, and
   determines whether during the first and second interventional procedures the navigation is performed along the same path based on the maximized similarity measure.

8. The navigation system as defined in claim 1, further comprising an inner structure providing unit for providing the anatomical structure of the living being, wherein the display further displays the anatomical structure of the living being from an entry location of the interventional device, at which the interventional device has entered the living being in the second interventional procedure, to a location of a tip of the interventional device as indicated by the second position and shape of the interventional device.

9. The navigation system as defined in claim 1, wherein the position and shape determining unit determines and stores in the first interventional procedure the position and shape of a first interventional device as the stored first position and shape and to determine in the second interventional procedure the position and shape of a second interventional device as the second position and shape, and wherein the navigation device enables navigation of the second interventional device during the second interventional procedure.

10. An interventional system for applying an interventional procedure to a living being, the interventional system comprising:
   an interventional device for performing the interventional procedure, and
   a navigation system for navigating the interventional device to the target region within the living being as defined in claim 1.

11. The navigation system as defined in claim 1, wherein the anatomical structure comprises a vascular structure.

12. The navigation system as defined in claim 1, wherein the anatomical structure comprises a pulmonary structure.

13. A non-transitory computer readable medium including instructions which, when executed by a computer, cause the computer to perform a method for enabling a user to navigate an interventional device to a target region within a living being, including:

determining and storing a first position and shape of the interventional device within the living being when the interventional device reaches the target region during a first interventional procedure using optical shape sensing;

continuously determining a second position and shape of the interventional device within the living being during a subsequent second interventional procedure using optical shape sensing; and displaying simultaneously the stored first positon and shape of the interventional device and second position and shape of the interventional device enabling navigation by the user of the interventional device along a same path to the target region, selected from a plurality of available paths through an anatomical structure, during the second interventional procedure as during the first interventional procedure by matching the second position and shape with the first position and shape, wherein the anatomical structure defines at least one branch point physically separating the available paths.

14. The non-transitory computer readable medium as defined in claim 13, wherein the anatomical structure comprises a vascular structure.

15. The non-transitory computer readable medium as defined in claim 13, wherein the anatomical structure comprises a pulmonary structure.

\* \* \* \* \*